US012734146B2

(12) United States Patent
Nag et al.

(10) Patent No.: US 12,734,146 B2
(45) Date of Patent: Sep. 15, 2026

(54) COBALT-PORPHYRIN COMPLEXES FOR THE INACTIVATION OF THE BIOLOGICAL ACTIVITY OF OPIOIDS

(71) Applicant: The Government of the United States of America, as represented by the Secretary of the Navy, Arlington, VA (US)

(72) Inventors: Okhil Nag, Alexandria, VA (US); D. Andrew Knight, New Orleans, LA (US); James B. Delehanty, Washington, DC (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 977 days.

(21) Appl. No.: 17/676,931

(22) Filed: Feb. 22, 2022

(65) Prior Publication Data

US 2022/0257553 A1 Aug. 18, 2022

Related U.S. Application Data

(63) Continuation-in-part of application No. 16/837,342, filed on Apr. 1, 2020, now Pat. No. 11,744,834.

(60) Provisional application No. 62/829,140, filed on Apr. 4, 2019.

(51) Int. Cl.

| | |
|---|---|
| ***A61K 31/28*** | (2006.01) |
| ***A61K 9/14*** | (2006.01) |
| ***A61K 47/69*** | (2017.01) |
| ***A61P 25/36*** | (2006.01) |

(52) U.S. Cl.
CPC ................ *A61K 31/28* (2013.01); *A61K 9/14* (2013.01); *A61K 47/6929* (2017.08); *A61P 25/36* (2018.01)

(58) Field of Classification Search
CPC ...... A61K 31/28; A61K 47/6929; A61P 25/36
See application file for complete search history.

(56) References Cited

FOREIGN PATENT DOCUMENTS

JP 2009-214092 A 9/2009

OTHER PUBLICATIONS (J. G. Cannon, Chapter Nineteen in Burger's Medicinal Chemistry and Drug Discovery, Fifth Edition, Volume I: Principles and Practice, Wiley-Interscience 1995. (Year: 1995).*
International Search Report and Written Opinion in PCT/US2020/026115 dated Jul. 16, 2020.
Grass, V. et al., "Reductive Electrochemistry of Rhodium Porphyrins. Disproportionation of Intermediary Oxidation States", Journal of the American Chemical Society, 1997, vol. 119, No. 15, pp. 3536-3542.
Fukushima, K. et al., "Synthesis and properties of Rhodium (III) porphyrin cyclic tetramer and cofacial dimer", Inorganic chemistry, 2003, vol. 42, No. 10, pp. 3187-3193.
Johnson, B. J. et al., "Porphyrin-embedded silicate materials for detection of hydrocarbon solvents", Sensors, 2011, vol. 11, No. 1, pp. 886-904.
Zhang., Y.-H. et al., "Raman and infrared spectral study of meso-sulfonatophenyl substituted porphyrins (TPPSn, n=1, 2A, 2O, 3, 4)", Spectrochimica Acta Part A: Molecular and Biomolecular Spectroscopy, 2003, vol. 59, No. 1, pp. 87-101.
Miyachi, M. et al., "Bio-inspired photoresponse of porphyrin-attached gold nanoparticles on a field-effect transistor", Biochimica et Biophysica Acta (BBA)—Bioenergetics, 2014, vol. 1837, No. 9, pp. 1567-1571.

* cited by examiner

*Primary Examiner* — Marcos L Sznaidman
(74) *Attorney, Agent, or Firm* — US Naval Research Laboratory; Fariborz Moazzam

(57) ABSTRACT

A cobalt-loaded porphyrin complex, comprising the porphyrin (meso-tri(4-sulfonatophenyl) mono(4-carboxyphenyl) porphine ($C_1S_3TPP$)) with coordinated with cobalt, effectively neutralizes the biological activity of opioids.

4 Claims, 5 Drawing Sheets

COBALT-PORPHYRIN COMPLEXES FOR THE INACTIVATION OF THE BIOLOGICAL ACTIVITY OF OPIOIDS

CROSS-REFERENCE TO RELATED APPLICATIONS

This Application claims the benefit as a continuation-in-part of U.S. patent application Ser. No. 16/837,342 filed on Apr. 1, 2020 which in turns claims the benefit of U.S. Provisional Patent Application No. 62/829,140 filed Apr. 4, 2019, the entirety of each of which is incorporated herein by reference.

FEDERALLY-SPONSORED RESEARCH AND DEVELOPMENT

The United States Government has ownership rights in this invention. Licensing inquiries may be directed to Office of Technology Transfer, US Naval Research Laboratory, Code 1004, Washington, D.C. 20375, USA; +1.202.767.7230; techtran@nrl.navy.mil, referencing NC 110705-US3.

BACKGROUND

The abuse of synthetic opioids has reached epidemic proportions on a worldwide scale, resulting in a major public health crisis [see ref. 1]. The potential weaponization of synthetic opioids on the battlefield also exists. The very real prospect of this scenario is highlighted by the 2002 incident in a Moscow theater where Russian Special Forces deployed a chemical aerosol containing a mixture of two highly potent synthetic opioid (fentanyl) derivatives: carfentanil and remifentanil against Chechen terrorists [2]. The aerosolized form of the opioids coupled with inadequate medical response resulted in 125 deaths.

Developed as a sedative for pain relief, synthetic opioids cause the depression of the respiratory system and psychomotor impairment. Acute administrations of opioids can result in overdose and death. The current state of the art for the treatment of opioid overdose is naloxone (NARCAN®), a competitive opioid receptor antagonist that has been in use since 1971. Naloxone's function is two-fold: (1) it competes with the opioid for binding to the opioid receptor and (2) it displaces opioid that is already bound to the receptor. In this capacity, naloxone decreases the activation of the intracellular opioid receptor signaling pathway while allowing the body to naturally clear the opioid through Phase I (oxidation) detoxification pathways (by cytochrome P450 enzymes in the liver). Because naloxone merely competes with and displaces bound opioid from the receptor, it often requires the administration of multiple doses until the body is able to clear the opioid from the system. In some instances, the effect of the opioid overdose cannot be overcome, even with repeated dosing. Further, because naloxone interacts directly with the opioid receptor, cessation of its usage can induce withdrawal symptoms in response to naturally-occurring opioids. Additionally, the expression of new opioid receptors as a result of habitual opioid use can render patients refractory to naloxone treatment due the overexpression of opioid receptors.

A need exists for alternative treatment for opioid overdose.

BRIEF SUMMARY

The invention involves a cobalt-loaded porphyrin complex which is generated by loading the porphyrin (meso-tri (4-sulfonatophenyl) mono(4-carboxyphenyl)porphine ($C_1S_3TPP$)) with a cobalt compound such as cobalt chloride hexahydrate.

In one embodiment, a material includes the porphyrin (meso-tri(4-sulfonatophenyl) mono(4-carboxyphenyl)porphine ($C_1S_3TPP$)) coordinated with cobalt.

In a further embodiment, a medicament includes the porphyrin (meso-tri(4-sulfonatophenyl) mono(4-carboxyphenyl)porphine ($C_1S_3TPP$)) coordinated with cobalt in conjunction with a pharmaceutically-acceptable carrier.

In yet another embodiment, a method of making the porphyrin (meso-tri(4-sulfonatophenyl) mono(4-carboxyphenyl)porphine ($C_1S_3TPP$)) coordinated with cobalt includes contacting $C_1S_3TPP$ with a cobalt compound.

In a still further embodiment, a method of treatment includes identifying a patient known or suspected of being in a condition of opioid overdose, and providing the patient with a medicament including the porphyrin (meso-tri(4-sulfonatophenyl) mono(4-carboxyphenyl)porphine ($C_1S_3TPP$)) coordinated with cobalt.

In additional embodiments, the cobalt-coordinated porphyrin is in a state of being conjugated to the surface of a nanoparticle (such as a gold nanoparticle).

BRIEF DESCRIPTION OF THE DRAWINGS

FIG. 2A shows adduct formed from oxidative dealklylation of fentanyl at m/z=562.337 (arrow) and FIG. 2B shows adduct formed from simple dealkylation of fentanyl at m/z=548.332 (arrow).

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

The invention comprises a cobalt-loaded porphyrin complex (referred to herein as "cobalt complex" or "Co—$C_1S_3$TPP complex") that effectively neutralizes the biological activity of naturally-occurring and synthetic opioids. This occurs with greater efficacy than the rhodium-loaded porphyrin complex ("rhodium complex") described in related U.S. Patent Application Publication No. 2020/0316085. The cobalt complex, when incubated with opioids under physiological conditions, results in the disappearance of fentanyl (used as a representative target synthetic opioid) through a heretofore unreported mechanism of the formation of fentanyl-Co breakdown adduct products. Moreover, in a tissue culture model system of opioid receptor activation, the cobalt complex inhibits fentanyl activation of the μ opioid receptor ~42% better than the rhodium complex.

It is expected that delivery of the cobalt complex to a patient known or suspected of suffering an opioid overdose might be effective to ameliorate the effects of the overdose. Thus, a medicament is contemplated comprising the cobalt complex in conjunction with a pharmaceutically-acceptable carrier.

Examples

Figure 1:
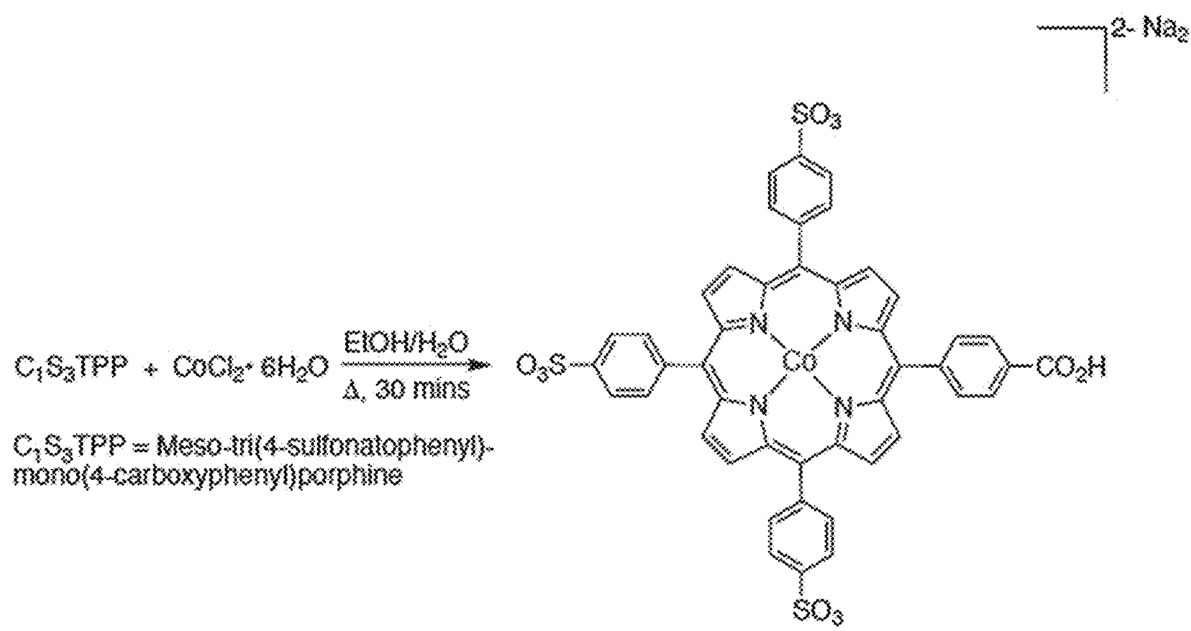
FIG. 1 illustrates a cobalt-porphyrin complex (Co-TPP) and the generation thereof by loading the porphyrin (meso-tri(4-sulfonatophenyl) mono(4-carboxyphenyl)porphine ($C_1S_3TPP$)) with cobalt chloride hexahydrate.

The Co-TPP complex was prepared by loading the porphyrin (meso-tri(4-sulfonatophenyl) mono(4-carboxyphenyl)porphine ($C_1S_3$TPP)) with cobalt chloride hexahydrate generally following a procedure previously described in the literature which involved a different porphyrin, X. Fu and B. B. Wayland, J. Am. Chem. Soc., 2004, 126, 2623, incorporated herein by reference for disclosing a technique for preparing a metal/porphyrin complex. As indicated in FIG. 1, incubation in ethanol/water for 30 minutes resulted in formation of the complex.

Figure 2A:
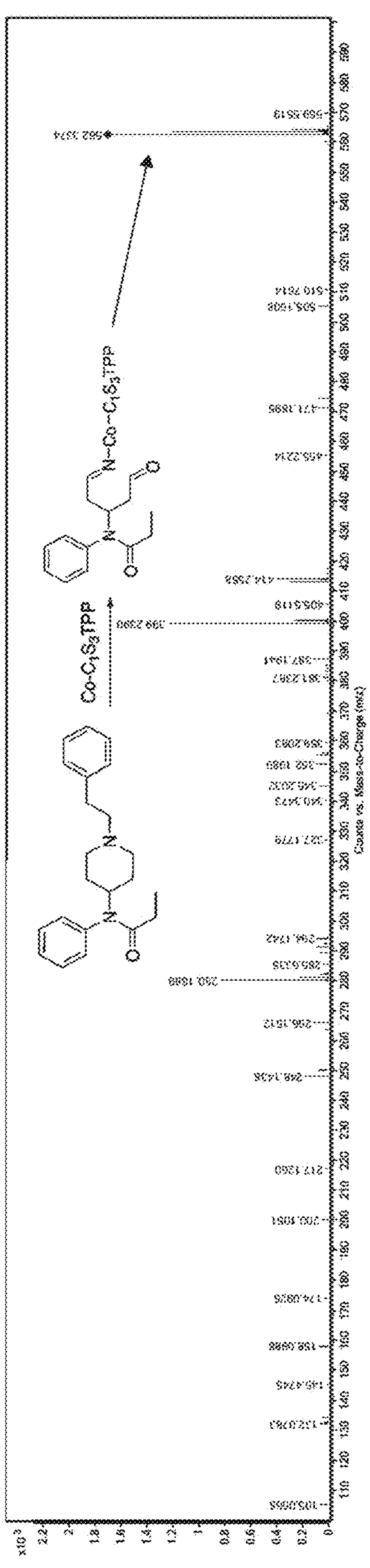
FIGS. 2A and 2B provide mass spectroscopic (MS) analysis of fentanyl incubated with Co-TPP showing the proposed mechanism for Co—$C_1S_3TPP$ removal of fentanyl and mass spectrum showing putative breakdown product adducts from extratcted ion chromatogram. Co—$C_1S_3TPP$ was incubated with fentanyl at 1:5 ratio for 64 hr at 37° C.
Figure 2B:
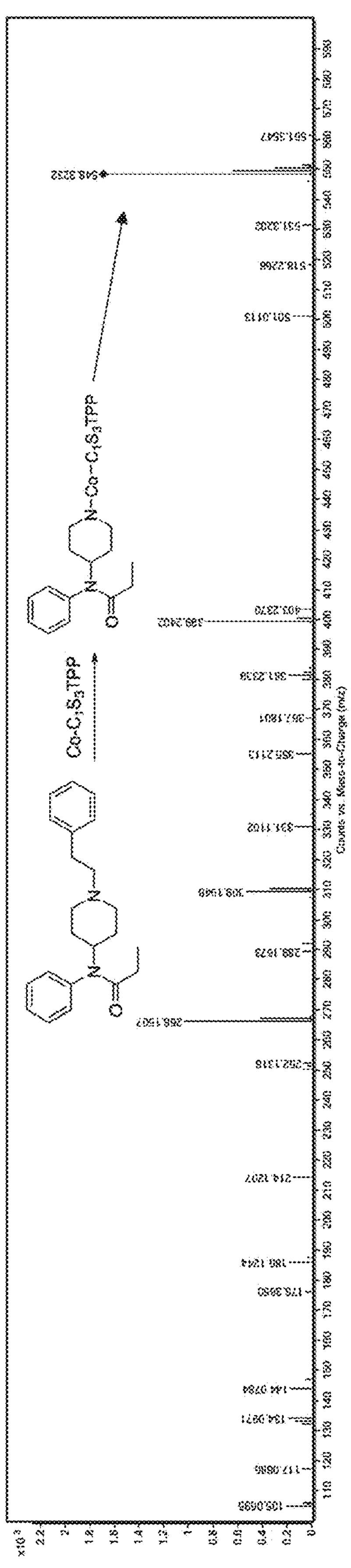

The interaction of the Co—$C_1S_3$TPP complex with fentanyl was first characterized using mass spectroscopy (MS) to determine the speciation of the products generated after Co-TPP was incubated with fentanyl (at 1:5 ratio) after 64 h at 37° C. FIGS. 2A and 2B show the results of MS analysis after fentanyl was incubated with the Co—$C_1S_3$TPP complex (at 1:5 ratio) for 64 h at 37° C. The data show the disappearance of fentanyl (as tracked by quantifying the molecular weight peak of fentanyl) and the appearance of a fentanyl: Co—$C_1S_3$TPP adduct (m/z=562.337) formed from oxidative dealkylation of fentanyl (FIG. 2B). FIG. 2*b* shows the formation of a fentanyl: Co—$C_1S_3$TPP adduct (m/z=548.332) formed from simple dealkylation of fentanyl. The formation of either adduct product results in the disappearance of the fentanyl molecular weight peak in this analysis.

Figure 3:
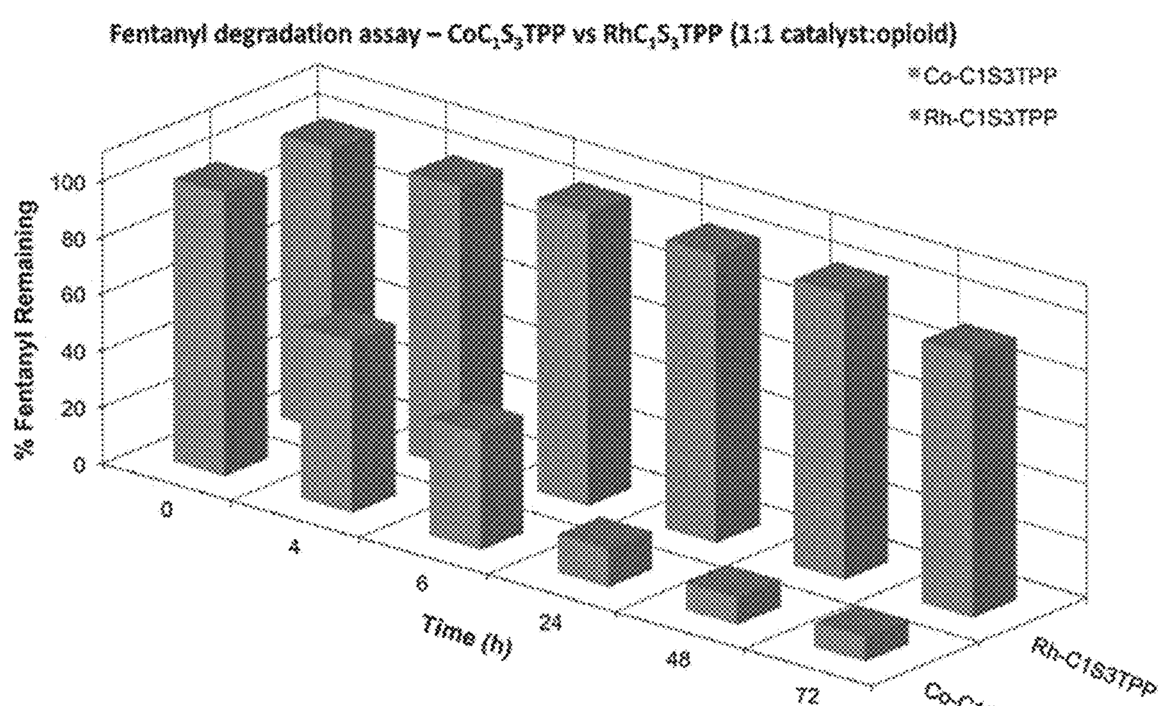
FIG. 3 shows a comparative MS analysis of fentanyl incubated with metal-porphyrins complexes at a 1:1 ratio. The cobalt complex was clearly more active than the rhodium complex. Percent fentanyl remaining was determined from mass spectral abundance peak area data (counts or arbitrary units) from the extracted ion chromatogram for the accurate mass of fentanyl FIG. 4 a comparative MS analysis of fentanyl incubated with metal-porphyrins complexes at a 5:1 ratio. The cobalt complex is clearly more active than the rhodium counterpart. Percent fentanyl remaining was determined from mass spectral abundance peak area data (counts or arbitrary units) from the extracted ion chromatogram for the accurate mass of fentanyl.
Figure 4:
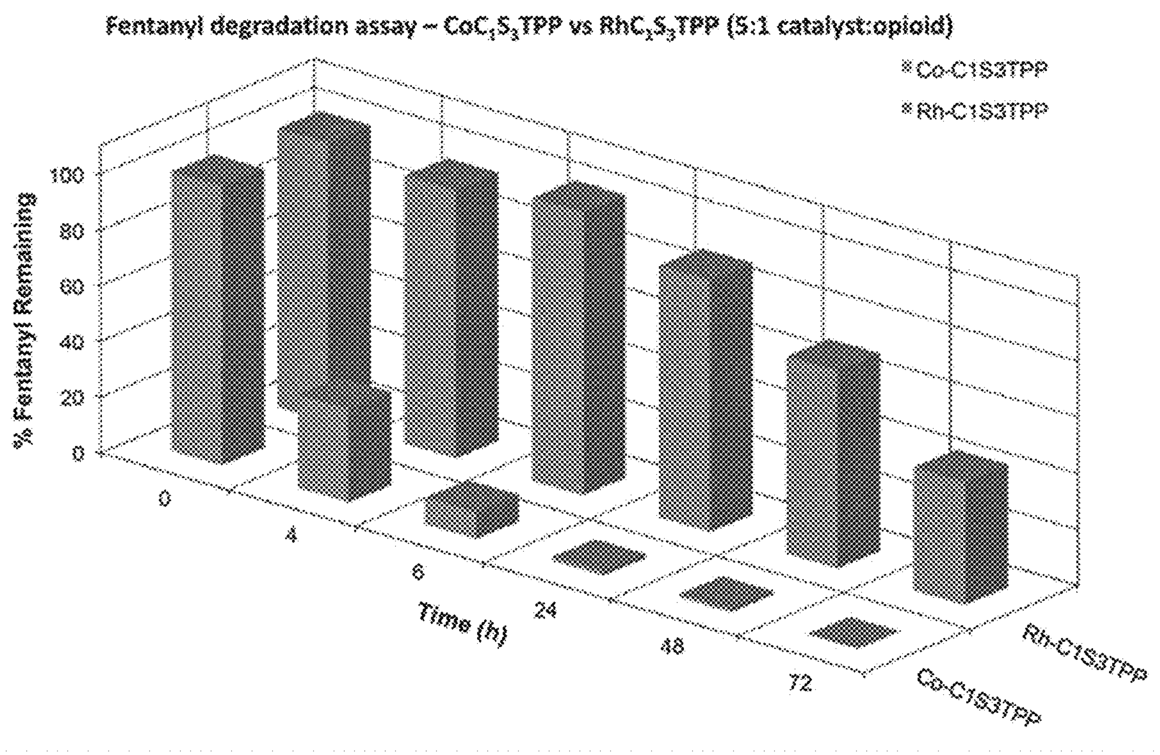

Co—$C_1S_3$TPP was incubated for 72 h at 37° C. to ascertain a time-resolved comparison of the disappearance of fentanyl mediated by either the Rh— or Co—$C_1S_3$TPP complex. FIG. 3 shows the results when the complexes were incubated at a 1:1 ratio. The Co—$C_1S_3$TPP complex clearly mediated a faster disappearance of fentanyl than did Rh-TPP over the 72 h time course. This effect was even further enhanced when the ratio of complex to fentanyl was increased to 5:1 (FIG. 4).

Figure 5:
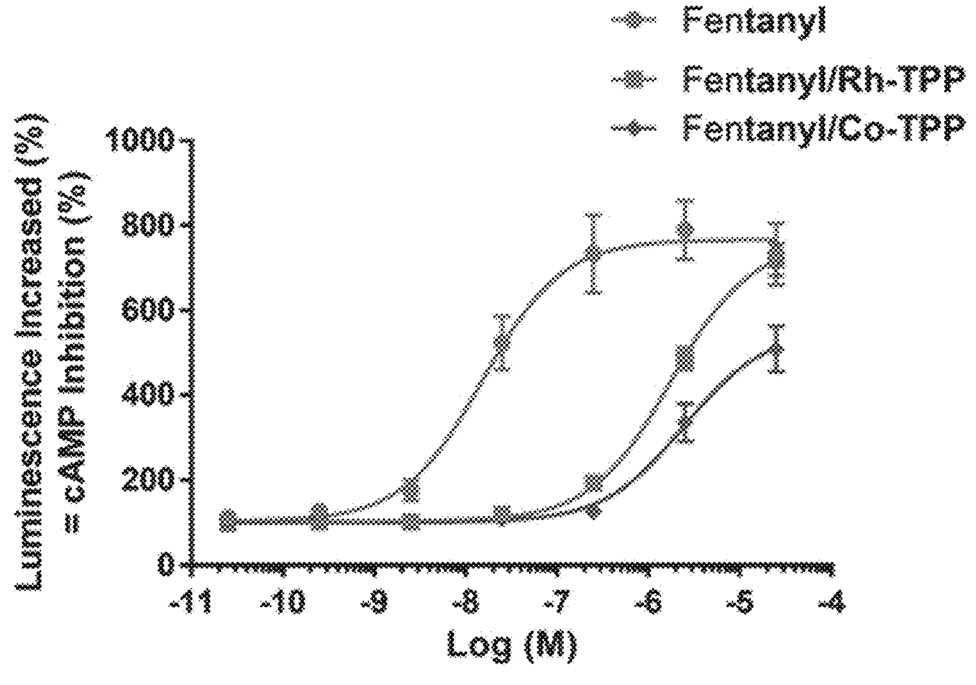
FIG. 5 plots the opioid activity of fentanyl incubated with Rh— and Co—$C_1S_3TPP$ complexes. Fentanyl (0.5 mM) was incubated at equimolar concentration with Rh—$C_1S_3TPP$ or Co—$C_1S_3TPP$ for 24 h at 37° C. The resulting products were assayed in a mu opioid receptor activation assay. Untreated fentanyl exhibits an IC50 of 15 nM while the IC50 of fentanyl incubated with Rh-TPP or Co—$C_1S_3TPP$ was 17 μm, respectively. Co—$C_1S_3TPP$ shows ~42% greater reduction in the activity of fentanyl compared to Rh—$C_1S_3TPP$.

FIG. 5 shows data from a classical cell-based opioid cellular signaling assay used to ascertain the biological activity of fentanyl after its incubation with the Rh— or Co—Co—$C_1S_3$TPP complexes. Chinese hamster ovary cells that stably express the mu opioid receptor were incubated with fentanyl alone or fentanyl that was treated with equimolar Rh—$C_1S_3$TPP or Co—$C_1S_3$TPP for 24 h. The ability of fentanyl to inhibit the formation of cyclic AMP is determined by measuring the cellular levels of free ATP. Here, an increase in photoluminescence intensity quantitatively tracks active fentanyl in a dose dependent manner. While Rh—$C_1S_3$TPP reduced the opioid activity of fentanyl~113-fold from an IC50 of 15 nM to 1.7 μM, Co—$C_1S_3$TPP reduced fentanyl activity ~160-fold to 2.4 μM. This corresponds to a 42% increase in the opioid-neutralizing activity fentanyl for the Co-TPP complex compared to the Rh—C1S3TPP complex.

Further Embodiments

It is expected that other metals besides could be used as a substitute in the porphyrin complex resulting in tailored activity.

The cobalt-porphyrin complex can be conjugated to and displayed on the surface of, or in the core of, various nanoparticles. It is expected that activity of the Co-TPP complex might be augmented in this fashion, just as was activity of the rhodium complex described in related U.S. Patent Application Publication No. 2020/0316085. Examples of these nanoparticles include, but are not limited to liposomes, gold nanoparticles, metal oxide particles, quantum dots, polymers, nucleic acids.

Other porphyrins could be used to generate the opioid-neutralizing complex.

Pharmaceutically acceptable carriers include carriers that do not themselves induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, and inactive virus particles. The carrier can comprise, consist of, consist essentially of, or be a saline solution, dextrose, albumin, a serum, or any of those disclosed in U.S. Pub. Nos.: 2008/0138408; 2009/0061003; 2009/0123530; 2010/0303901; 2012/0034198; and 2016/0008290 and U.S. Pat. Nos. 6,992,066; 5,785,973; 7,485,294; 8,088,734; 8,753,645; 8,808,733; and 8,858,998.

The compositions typically will contain pharmaceutically acceptable vehicles, such as water, saline, glycerol, ethanol, etc. Additionally, auxiliary substances, such as wetting or emulsifying agents, pH buffering substances, preservatives, and the like, may be included in such vehicles.

Typically, the compositions are prepared as injectables, either as liquid solutions or suspensions; solid forms suitable for solution in, or suspension in, liquid vehicles prior to injection may also be prepared. The preparation also may be emulsified or encapsulated in liposomes. Solutions for infusion or injection may be prepared in a conventional manner, e.g. with the addition of preservatives such as p-hydroxybenzoates or stabilizers such as alkali metal salts of ethylenediamine tetraacetic acid, which may then be transferred into fusion vessels, injection vials or ampules. Alternatively, the compound for injection may be lyophilized either with or without the other ingredients and be solubilized in a buffered solution or distilled water, as appropriate, at the time of use. Non-aqueous vehicles such as fixed oils and ethyl oleate are also useful herein.

In cases where intramuscular injection is the mode of administration, an isotonic formulation can be used. Generally, additives for isotonicity can include sodium chloride, dextrose, mannitol, sorbitol and lactose. In some cases isotonic solutions such as phosphate buffered saline are preferred. Stabilizers include glycerol, gelatin and albumin which may be included in the formulation. In some embodiments, a vasoconstriction agent is added to the formulation.

Additional pharmaceutical methods may be employed to control the duration of action. Controlled release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, polylactic acid or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly (methylmethacylate)-microcapsules, respectively, or in colloidal drug delivery systems, for example, liposomes, albumin microspheres, microemulsions, nanoparticles, and nanocapsules or in macroemulsions.

Concluding Remarks

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

[1] H. Hedegaard et al. (2018) "Drugs Most Frequently Involved in Drug Overdose Deaths: United States, 2011-2016." *National Vital Statistics Reports* 67: 1-13.

[2] J. R. Riches et al. (2012) "Analysis of Clothing and Urine from Moscow Theatre Siege Casualties Reveals Carfentanil and Remifentanil Use" *Journal of Analytical Toxicology* 36:647-656.

What is claimed is:

1. A material comprising the porphyrin (meso-tri(4-sulfonatophenyl) mono(4-carboxyphenyl)porphine ($C_1S_3TPP$)) coordinated with cobalt, wherein the porphyrin has the following structure:

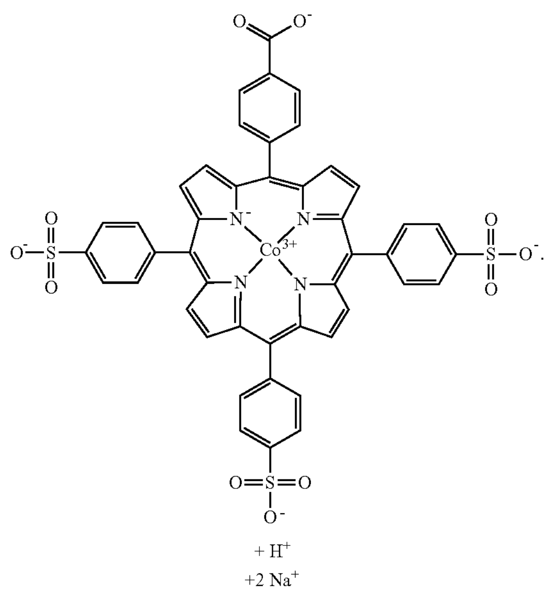

2. The material of claim 1, wherein the cobalt-coordinated porphyrin is in a state of being conjugated to the surface of a nanoparticle.

3. A medicament comprising:

the porphyrin (meso-tri(4-sulfonatophenyl) mono(4-carboxyphenyl)porphine ($C_1S_3TPP$)) coordinated with cobalt, wherein the porphyrin has the following structure:

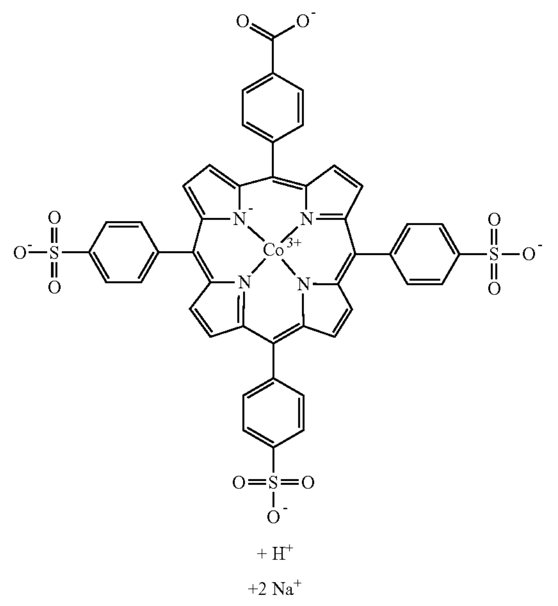

and a pharmaceutically-acceptable carrier.

4. The medicament of claim 3, wherein the cobalt-coordinated porphyrin is in a state of being conjugated to the surface of a nanoparticle.

* * * * *